(12) United States Patent
Bieniarz et al.

(10) Patent No.: US 6,503,528 B1
(45) Date of Patent: Jan. 7, 2003

(54) POLYMERIC COMPOSITIONS AND A METHOD OF MAKING THE SAME

(75) Inventors: Christopher Bieniarz, Highland Park, IL (US); Amy Jo Sanders, Massillon, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/444,478

(22) Filed: Nov. 19, 1999

(51) Int. Cl.⁷ .................................................. A61F 2/02
(52) U.S. Cl. ..................................... 424/426; 514/772.3
(58) Field of Search ........................ 424/426; 514/772.3

(56) References Cited

U.S. PATENT DOCUMENTS

| | | | |
|---|---|---|---|
| 4,629,621 A | 12/1986 | Snipes | |
| 4,757,128 A | 7/1988 | Domb et al. | 528/271 |
| 4,789,724 A | 12/1988 | Domb et al. | 528/176 |
| 4,857,311 A | 8/1989 | Domb et al. | 424/78 |
| 4,888,176 A | 12/1989 | Langer et al. | 424/426 |
| 4,891,225 A * | 1/1990 | Langer et al. | 424/428 |
| 4,906,474 A | 3/1990 | Langer et al. | 424/428 |
| 5,010,167 A | 4/1991 | Ron et al. | 528/328 |
| 5,122,367 A | 6/1992 | Ron et al. | 424/80 |
| 5,171,812 A | 12/1992 | Domb | 526/318.2 |
| 5,270,419 A | 12/1993 | Domb | 526/318.2 |
| 5,393,765 A | 2/1995 | Infeld et al. | |
| 5,886,026 A | 3/1999 | Hunter et al. | |

FOREIGN PATENT DOCUMENTS

| | | |
|---|---|---|
| EP | 0 052 916 | 6/1982 |
| GB | 2 260 080 | 4/1993 |
| WO | 93/20134 | 10/1993 |
| WO | 95/35097 | 12/1995 |

OTHER PUBLICATIONS

Park, et al., "Effects of Model Compounds with Varying Physicochemical Properties on Erosion of Polyanhydride Devices", *Journal of Controlled Release*, vol. 40, 1996, pp. 111–121.

Domb, et al., Solid–State and Solution Stability of Poly(anhydrides) and Poly(esters), *Macromolecules*, vol. 22 (5), pp. 2117–2122, 1989.

* cited by examiner

*Primary Examiner*—Carlos Azpuru
(74) *Attorney, Agent, or Firm*—B. Gregory Donner (57) ABSTRACT

The invention relates to a bioerodible polymeric composition, a method of making such a composition, and a controlled delivery device comprising the composition.

22 Claims, 4 Drawing Sheets

POLYMERIC COMPOSITIONS AND A METHOD OF MAKING THE SAME

TECHNICAL FIELD OF THE INVENTION

The invention relates to a bioerodible polymeric composition, a method of making such a composition, and a controlled delivery device comprising the composition.

BACKGROUND OF THE INVENTION

Bioerodible polymeric compositions are well-known materials useful for administering pharmaceutical medicaments. One advantage of a drug delivery system prepared from a bioerodible polymer is that the polymer erodes in an aqueous environment. As the polymer erodes, the drug is released from the polymeric matrix. The erosion of the polymer in the aqueous physiological environment of a mammal during the concomitant release of the drug obviates the need to remove the delivery system once the medicament is expended.

The rate of drug release from the matrix has been determined to have a direct relationship with the rate of degradation of the polymeric material. Traditionally, it has been understood that the drug release from the matrix is triggered by the hydrolysis of the polymer. The drug concomitantly diffuses away from the polymeric matrix as the polymeric chains of the matrix hydrolyze. For this reason, efforts related to modifying the drug release from and the degradation rate of the polymeric composition have focused on protecting the polymer against hydrolysis.

It is widely accepted that changes in the structure of the polymeric backbone are necessary to modify the hydrophobicity properties of the polymer. Mark et al., *Encyclopedia of Polymer Science and Engineering*, Vol. 22, John Wiley & Sons, 1985. Accordingly, attempts to improve the release profile of polymeric matrices have been directed toward altering the molecular weight of the polymeric backbone.

U.S. Pat. No. 4,857,311, for example, describes polyanhydrides with a uniform distribution of aliphatic and aromatic residues. The uniform distribution of aliphatic and aromatic residues in the chain allows for uniform degradation at a rate useful for controlled bioactive delivery.

U.S. Pat. No. 4,888,176 describes the preparation of high molecular weight polyanhydride controlled delivery devices.

U.S. Pat. No. 4,789,724 describes the preparation of very pure anhydride co-polymers of aromatic and aliphatic diacids.

U.S. Pat. No. 5,010,167 describes a biodegradable poly (amide- and imide-co-anhydride) prepared by the co-polymerization of amido- or imido-dicarboxylic acid monomers with other dicarboxylic acids.

U.S. Pat. No. 5,171,812 describes a polyanhydride synthesized from monomers prepared by linking two or more unsaturated aliphatic carboxylic acids.

However, the rate of release at any given temperature is crucially dependent on the molecular weight of the polymeric constituents of the drug delivery matrix. Even under strictly anhydrous conditions, the bioerodible polymer undergoes a decrease in the average molecular weight. This phenomenon is inconsistent with a hydrolytic degradation mechanism.

Abraham Domb and Robert Langer have proposed that the anhydrous degradation of a polymeric matrix is a consequence of self-depolymerization of the polymeric backbone via inter- and intramolecular interchange. *Macromolecules*, 22, 2117–2122 (1989). For example, in its lowest Gibbs free energy geometry, the inter- and intrachain alignment of the carbonyl groups of a polyanhydride matrix allows for nucleophilic attack of the anhydride oxygen on the carbonyl carbon of the adjacent polymeric chain. The self-depolymerization mechanism leads to the gradual loss of the average molecular weight of the polymer. The decrease of the molecular weight of the polymer directly affects the rate at which the drug in the matrix diffuses away from the polymeric matrix. The self-depolymerization mechanism is believed to occur independently of the hydrolytic degradation mechanism.

The recognition of a self-depolymerizing mechanism in the bioerodible matrices provides new possibilities for modifying the degradation rate in a polymeric matrix. In particular, one or more pharmaceutically acceptable additives can be blended with the polymer to provide a new polymeric material having either an increased or a decreased rate of degradation relative to the degradation rate of the polymeric starting material.

There is no precedent of modifying the rate of degradation in a bioerodible polymeric composition by blending the polymer with additive. In one instance, U.S. Pat. No. 5,122,367 describes a controlled release implant claiming that sugar is a stabilizing agent for the release of an active growth hormone from the implant. However, the sugar is co-lyophilized with the growth hormone to affect release of the hormone. The co-lyophilization of the sugar with the growth hormone stabilizes the hormone. There is no description of the sugar having any effect on the degradation of the polymeric matrix.

Therefore, there remains a need for providing a bioerodible polymeric matrix having a reproducible drug release rate. It would be beneficial to have a polymeric matrix in which the degradation rate of the matrix can be increased or decreased in a reproducible manner when compared with the degradation rate of the starting polymer.

SUMMARY OF THE INVENTION

The invention relates to a bioerodible polymeric composition and a method for preparing the same. The bioerodible polymer comprises covalently bonded repeating units, commonly referred to as monomers. The polymer is blended with a pharmaceutically acceptable additive to afford a polymer having modified degradation characteristics. The resulting composition possesses the characteristics of hydrophobicity, stability, strength, flexibility, organic solvent solubility, low melting point and an appropriate degradation profile suitable for being incorporated into a controlled delivery device.

One embodiment of the composition comprises the bioerodible polymer and an accelerant additive. The accelerant additive is a compound having a hydrophilic and a hydrophobic domain, such as in a detergent. In this embodiment, the hydrophilic and the hydrophobic domains of the additive associate with the respective hydrophilic and the hydrophobic domains of the polymer. The resulting composition exhibits an increased rate of polymer degradation. The increased rate of degradation in the polymer can be beneficial for preparing a delivery device for medicament having a more rapid rate of controlled release when compared with a device prepared from the same polymer, but without additives.

Another embodiment of the composition comprises the bioerodible polymer and a retardant additive. The retardant additive is a compound that is chemically non-reactive in the polymeric matrix environment. The chemically non-reactive additive shields the inter- and intramolecular nucleophilic attack of the functional groups in the polymeric chain. The presence of the additive retards the rate of degradation in the polymer, allowing for the effect of delayed release of the medicament.

The method of the invention comprises blending a bioerodible polymer with a pharmaceutically acceptable additive. The method provides a new bioerodible polymer having modified degradation characteristics. The method can be used to prepare bioerodible polymeric compositions having a repeatable rate of degradation that is either increased or decreased when compared to the starting polymer.

The steps for preparing the polymeric composition comprise:

(a) melting the bioerodible polymer at a temperature above the glass transition temperature of the polymer; and (b) adding and blending a pharmaceutically acceptable additive to the polymer.

The polymer blend can be extruded, melted and mixed to provide the desired polymeric matrix. The blend can also be molded under adequate temperature and pressure conditions, for example by injection or compression molding techniques, to provide a polymeric composition of the desired shape.

The composition can be modified to provide a controlled delivery device for a pharmaceutical medicament. The controlled delivery device will be suitable for administering practically any medicament. The controlled delivery device will exhibit a reproducible, modified rate of degradation when compared to the degradation rate of the starting polymer.

DETAILED DESCRIPTION OF THE INVENTION

As used herein the term "polymer" refers to a compound formed by covalently bonding one or more repeating chemical units. The units are commonly referred to as monomers. Polymers of the invention include homopolymers and co-polymers. A homopolymer as used herein refers to a polymer having repeating units of a single monomer. Examples of monomer units are acids, diacids, alcohols, and the like. Acids include, but are not limited to, lactic acid (LA), sebacic acid (SA), erucic acid (EA), suberic acid (SA), adipic acid (AA), bis(p-carboxyphenoxy)methane (CPM), 1,2-bis(p-carboxyphenyoxy)propane (CPP), 1,6-bis(p-carboxyphenoxy)hexane (CPH), phenylenedipropionic acid (PDP), and the like. A co-polymer as used herein is produced by polymerization of two or more dissimilar monomers, for example sebacic acid and fatty acid dimer.

As used herein the term "pharmaceutically acceptable additive" refers to any substance or excipient that can be incorporated into a base material to accelerate or impede the inter- and intrachain reaction in a polymeric matrix having the chemical and physical qualities and properties appropriate for use in a pharmaceutical product. Pharmaceutically acceptable additives can be selected by a number of criteria, including reactive properties, molecular weight, hydrophilicity and/or hydrophobicity of the compound, and the like, to either accelerate or retard the rate of degradation. An extensive, but not exhaustive, list of pharmaceutical excipients can be found in the *Handbook of Pharmaceutical Excipients*, edited by Ainley Wade and Paul J. Weller, 2nd ed., American Pharmaceutical Association, 1994.

As used herein the term "accelerant additive" refers to a pharmaceutically acceptable additive as described above which interacts with the polymeric material to increase the rate of degradation in the polymeric material when compared to the degradation rate of the polymer without the additive. A preferred accelerant additive does not affect the biological activity of any medicament with which it is blended. Accelerant additives are typically detergents, which include, but are not limited to, esters of sorbitol and fatty acids. Examples of accelerant additives are sorbitan monooleate, sorbitan monostearate, sorbitan monolaurate, sorbitan trioleate, and the like.

As used herein the term "retardant additive" refers to a pharmaceutically acceptable additive as described above which interacts with the polymeric material to slow the rate of degradation when compared to the degradation rate of the polymer without the additive. A preferred retardant additive does not affect the biological activity of any medicament with which it is blended. Retardant additives can be any chemically non-reactive additive, which are, for example, paraffins (waxes), polyalkylene glycols, or polyalkylene oxides.

As used herein the term "chemically non-reactive additive" refers to an additive as defined above wherein the additive associates or co-aligns with one or more domains in the polyanhydride matrix. Such chemically non-reactive additives exhibit the described properties under stability of temperature, pressure, humidity, and other ambient conditions consistent with the storage of a bioerodible matrix. Examples of chemically non-reactive additives are paraffins, polyalkylene glycols, polyalkylene oxides, and the like.

Compositions

The polymer of the invention is one wherein the polymeric chains undergo degradation via inter- and intrachain nucleophilic attack or chemical interchange. The polymers are typically polyanhydride, polyester, polyorthoester, polyketones, or polycarbonates. The polymers comprise repeating monomers of carboxylic acids, dicarboxylic acids (diacids), and alcohols. The preferred polymers are polyanhydrides.

Homopolymers of the invention are those having a single repeating monomeric unit. A preferred homopolymer comprises the repeating monomers of linear or branched aliphatic dicarboxylic acids or aromatic acids. The preferred monomer can be represented, for example, by the structural formula:

wherein l is an integer between 5 and 200; and R is an aliphatic or aromatic hydrocarbon. Examples of anhydride polymers suitable for the invention are those polyanhydrides composed of the monomers of sebacic acid, erucic acid, suberic acid, adipic acid, bis(p-carboxyphenoxy)methane, 1,2-bis(p-carboxyphenyoxy)propane, 1,6-bis(p-carboxyphenoxy)hexane, and phenylenedipropionic acid.

Co-polymers of the invention have two or more types of monomers and can be represented by a formula:

wherein the sum of n and m is between 5 and 200, and R and R' are independently selected from aliphatic or aromatic hydrocarbon. A preferred co-polymer of the invention is prepared by co-polymerizing a monomeric unit derived from a dicarboxylic acid with a fatty acid dimer represented by the general formula:

wherein the variable j and k are integers other than zero, and j and k equal a constant value of 19. Co-polymerization can be accomplished by incorporating a desired ratio of the diacid and diacetylated prepolymers in anhydrous solvent and heating to reflux under high vacuum. Typically, it is preferred that about 1 to 2 portions of fatty acid prepolymer of the co-polymer is used for each portion of the dicarboxylic acid prepolymer by weight. The preferred co-polymer will have 1 portion of the fatty acid prepolymer for each portion of the dicarboxylic acid prepolymer by weight.

The polyanhydride can be randomized, repeating or block co-polymers of a suitable combination of the monomer units described above. Co-polymers are especially preferred when a randomized distribution of the monomeric units results in a uniformly distributed polyanhydride demonstrating uniform degradation.

The polymer can be prepared by methods known in the art, for example melt polycondensation. Melt polycondensation involves heating the dicarboxylic acid with an acetic anhydride reagent to prepare a diacetylanhydride prepolymer. The prepolymer is heated under vacuum to afford the polymer, see U.S. Pat. No. 4,789,724, for example, describing a process for preparing anhydride co-polymers by melt polycondensation.

A preferred method for preparing a polyanhydride co-polymer is illustrated in the following Scheme 1:

Scheme 1

As illustrated in Scheme 1, sebacic acid 1 is reacted with acetic anydride to form prepolymer 2, wherein n is an integer from 5 to 200. The fatty acid dimer 3, wherein j and k are integers, the sum of which is 19, is treated with acetic anhydride to form the corresponding prepolymer 4, wherein m is an integer from 5 to 200. Prepolymer 2 and prepolymer 4 are heated under vacuum to prepare the co-polymer 5, wherein the x:y is the molar ratio of the prepolymer 2 and the prepolymer 4, respectively, and t is the degree of polymerization. The preparation of 5 gives an acetic acid by-product, which can be removed by distillation at elevated temperatures. Further discussion regarding the preparation of anhydride co-polymers can be found in U.S. Pat. No. 4,789,724, which is herein incorporated by reference.

To ensure mutual miscibility of the polymers, the blend of two polymers will have a single glass transition temperature. The glass transition temperature ($T_g$) refers to the temperature range at which the vitrious or crystalline, glassy solid state changes to a viscous liquid state of the polymer. The glass transition temperature of the pure component polymer and the polymeric blend can be determined using Dynamic Mechanical Thermal Analysis (DMTA) or dynamic mechanical measurement, which is a technique well known in the art. A more thorough discussion of the glass transition temperature and the techniques suitable for determining $T_g$ can be found in Mark et al., *Encyclopedia of Polymer Science and Engineering*, 3rd ed., Vol. 7, John Wiley & Sons, 1987; and G. Allen et al., eds., *Comprehensive Polymer Science*, Pergamon Press, Vol. 5, 1989.

A miscible blend of the polymeric blend shows a single glass transition temperature. The additives yielding a "true blend", i.e. having a single $T_g$ as determined by DMTA standards, were considered in the invention. Preferably the $T_g$ of the polymer, including homopolymers and co-polymers, is between −30° C. and 50° C. More preferably, $T_g$ is a temperature between about 25° C. and 35° C.

It is preferred that the polymers have an average molecular weight ($\overline{MW}$) from at least 10,000 grams per mole (g/mol) to 1,000,000 g/mol. Preferably, the polymer has an average molecular weight from about 20,000 g/mol to 500,000 g/mol. A more preferred range for the average molecular weight of the polymer is from about is 30,000 g/mol to 150,000 g/mol. Most preferably, the molecular weight of the polymer is about 50,000 g/mol. Average molecular weight for the polymer can be measured by gel permeation chromatography using polystyrene standards.

In one embodiment, the accelerant additive is one that readily associates with the respective hydrophilic and hydrophobic domains of the polymer when blended. A suitable additive will have both a hydrophilic domain and a hydrophobic domain. An illustration of the hypothetical interaction between one example of the accelerant additive, sorbitan monolaurate, and the polymeric chain can be found in FIG. 1.

Figure 1:
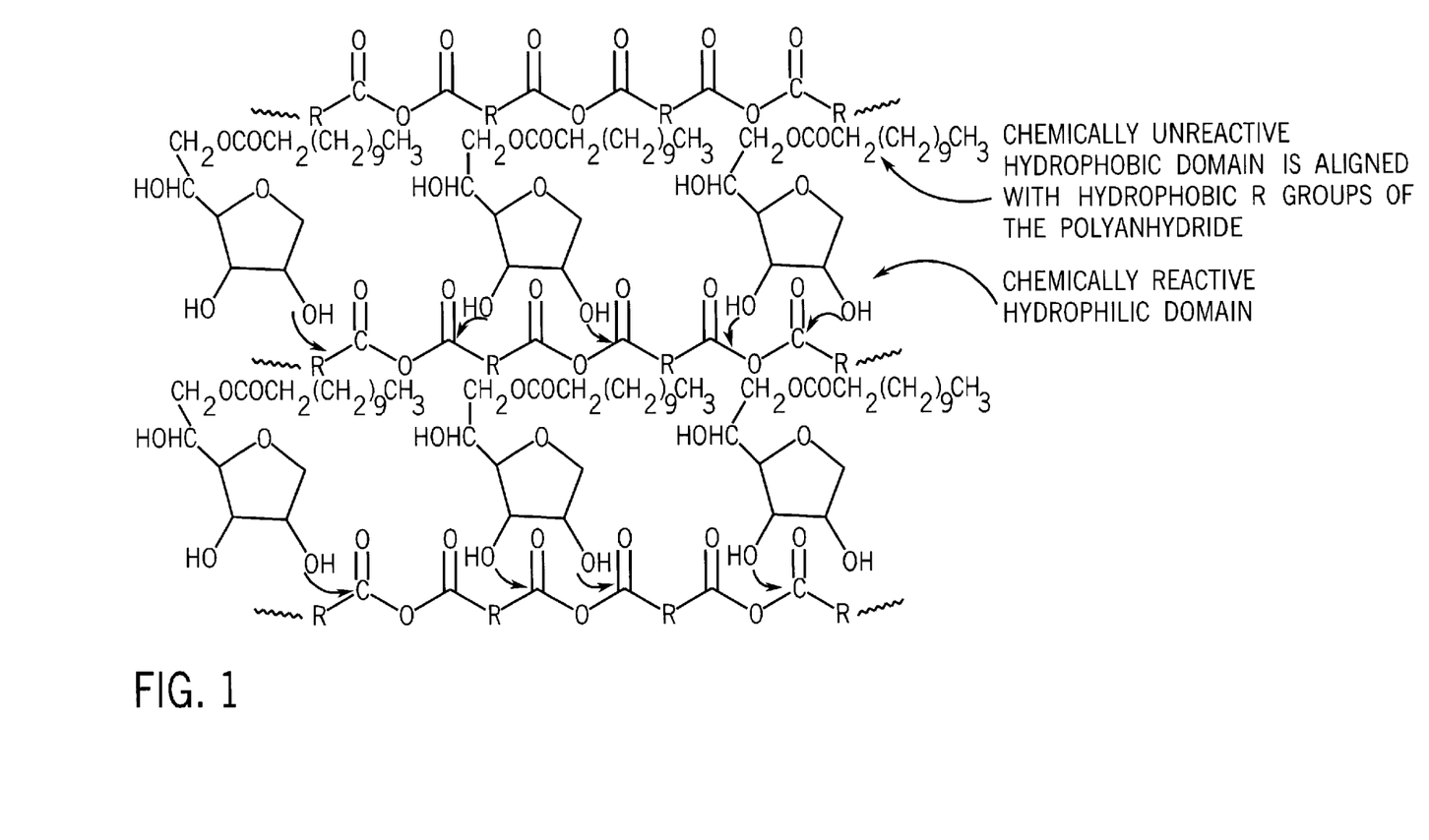
FIG. 1 is a schematic illustration of the hypothetical mechanism by which the accelerant additive may interact with the polymer. One example of an accelerant additive, sorbitan monolaurate, is shown in proximity with the chains of the polyanhydride matrix.

As shown in FIG. 1, the hydrophilic domain of the additive may associate with the less hydrophilic domain of the polymer. The hydrophobic domain of the additive associates with the more hydrophobic domain of the polymer.

A preferred additive for this embodiment is one where a hydrophilic domain of the additive is conjugated to a hydrophobic domain of the additive. Compounds of this type are typically detergents. The hydrophobic region of the additive is preferably an unreactive group, such as alkyl. Generally, the hydrophilic region is comprised of a reactive group, for example a carbohydrate group. Particularly preferred accelerant additives for the invention are esters of sorbitol and fatty acids, for example sorbitan monooleate, sorbitan monostearate, sorbitan monolaurate, sorbitan trioleate, and the like.

The polymer can be blended with a retardant additive to provide a composition of another embodiment. In this embodiment, the presence of the retardant additive in the composition decreases the rate of degradation in the polymer. The suggested hypothetical mechanism for the retardant effect of the additive is shown in FIG. 2.

Figure 2:
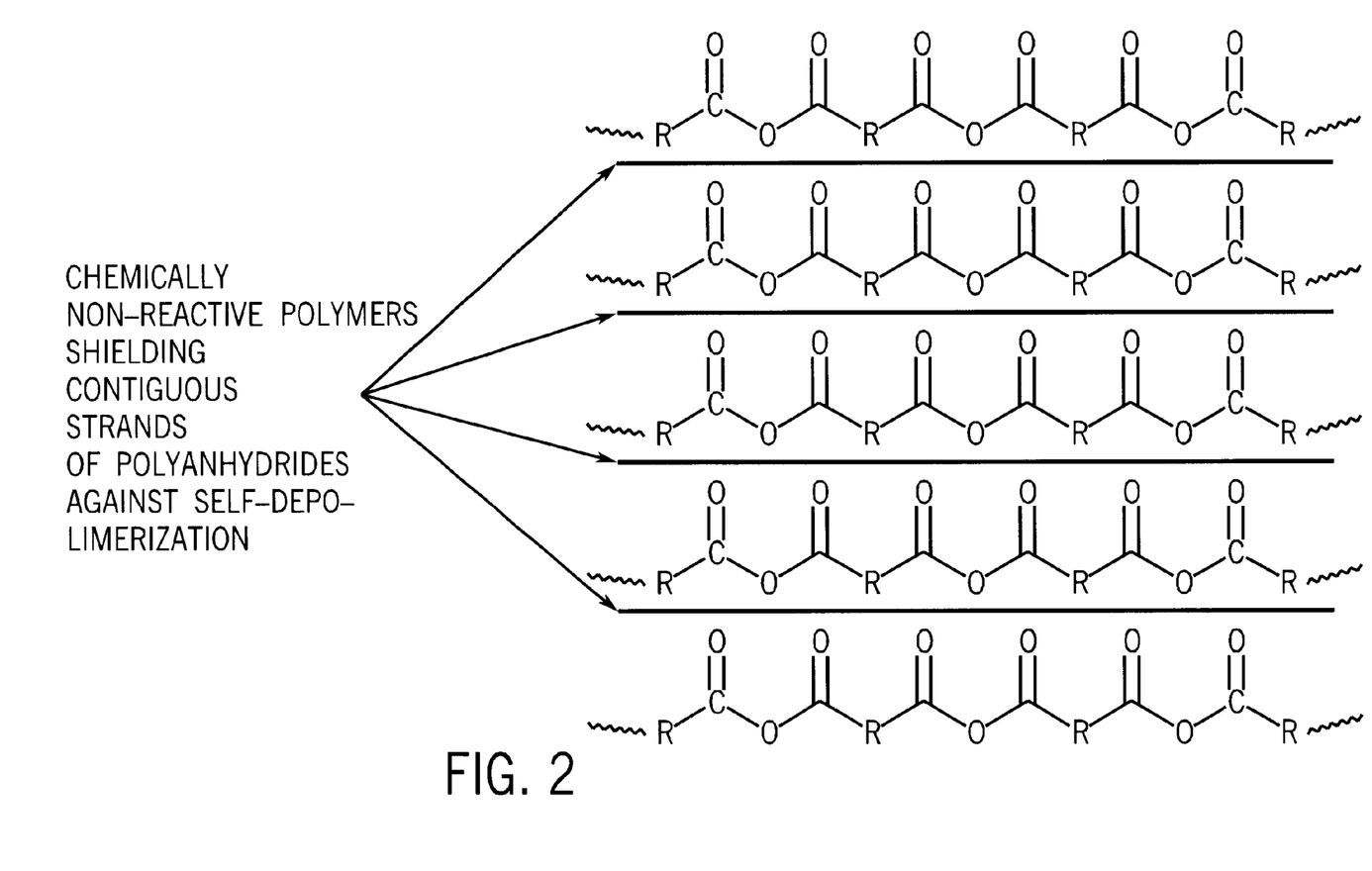
FIG. 2 is a schematic illustration of the hypothetical mechanism by which the retardant additive interacts with the polymer. The dark solid lines are representative of a chain of chemically non-reactive polymers between the chains of a polyanhydride matrix.

As illustrated in FIG. 2, the retardant additive intercalates between the adjacent, aligned chains of the polymeric matrix. The additive physically shields the nucleophilic attack of the carbonyl group on one chain of the polymer from the reactive group of another, and most likely adjacent, polymer chain. The shielding effect impedes the rate of depolymerization, which allows for the delayed release of the medicament from the polymer.

Generally, the retardant additive is a chemically non-reactive compound in the polymeric matrix environment. Preferred chemically non-reactive additives are waxes, or paraffins, polyalkylene glycols, polyalkylene oxides, and other pharmaceutically acceptable chemically non-reactive compounds. Examples of polyalkylene oxides suitable for the invention are polypropylene oxide, polyethylene oxide, and the like. Polyalkylene glycols suitable for the invention are polyethylene glycol and its derivatives, for example polyethylene glycol methyl ether, and the like.

The additive should be added in an amount sufficient to obtain the desired rate of degradation in the polymeric matrix. Preferably, the amount of additive for either accelerating or retarding the rate of degradation in the matrix is from about 1% to about 20% weight by weight relative to the weight of the matrix. The more preferred amount of the additive added is about 5% of the matrix, by weight.

When compared with the degradation rate of the polymeric matrix with no additives, the blend having the accelerant additive shows a reproducible, increased rate of degradation. Examples of the polymer with accelerant additive are compared with the polymer without additive in FIG. 3. The compositions having an accelerant additive require very low temperatures and controlled conditions of low humidity, i.e. dessicant conditions. The compositions may require storage conditions of temperatures less than −40° C. to provide additional stability to the matrix.

Figure 4:
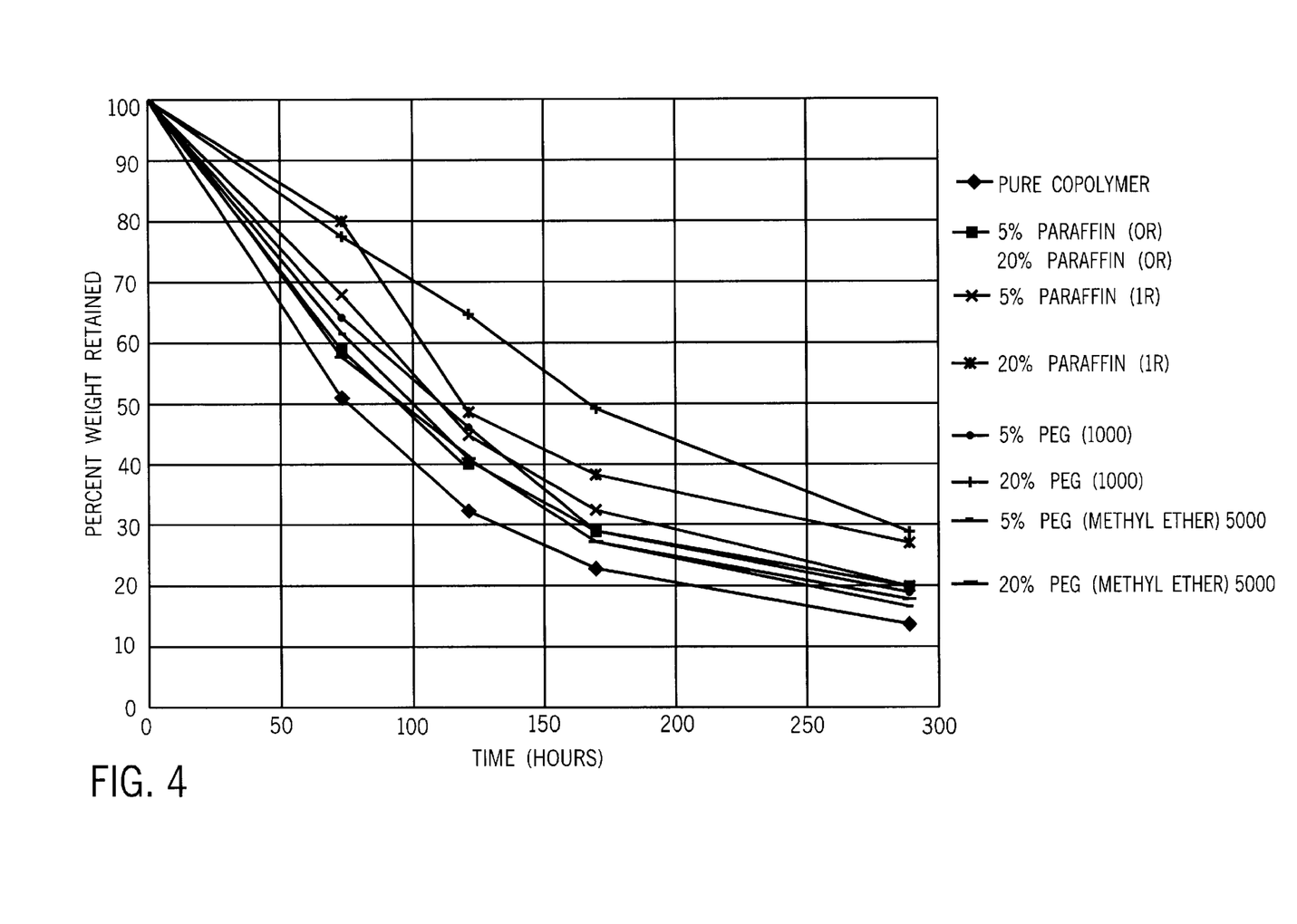
FIG. 4 is a graph illustrating the percent molecular weight retained of a pure polyanhydride co-polymer of a fatty acid dimer (FAD C44) and sebacic acid (SA) compared with co-polymer blends having various retardant additives as a function of time (in hours) under conditions of 25° C and 40% humidity.

The degradation rate of the starting polymer blended with the retardant additive shows a reproducible, decreased rate of degradation when compared with the polymer without additive. Comparison of exemplary blends having retardant additive with the polymer blend without additive is shown in FIG. 4. Whereas in a typical bioerodible material, the storage conditions require controlled conditions having low temperatures and low humidity, typically dessicant conditions, the additive used as a retardant can be blended with the polymer to provide additional stability to the matrix. The retardant effect of the additive in this embodiment improves the shelf life of the polymeric material when compared with the shelf life of the pure polymer.

The bioerodible composition can be prepared in accordance with the following steps:
(a) melting the bioerodible polymer at a temperature above the glass transition temperature of the polymer; and
(b) adding and blending a pharmaceutically acceptable additive to the polymer.

The polymer blend can be extruded, melted and mixed to provide the desired polymeric matrix. The blend can also be molded under adequate temperature and pressure conditions, for example by injection or compression molding techniques, to provide a polymeric composition of the desired shape.

The bioerodible polymer, additive and a drug can be intimately admixed to provide a pharmaceutically acceptable drug delivery device. The polymeric composition and the drug can be admixed in any convenient manner. Relative portions of the drug incorporated into the polymeric matrix can vary over a wide range depending on the activity of the molecule, the degradation rate of the polymer and the desired rate of drug release from the polymeric matrix. Preferred proportions for the invention can range from about 1 to about 50 parts by weight of the desired drug. Preferably, the matrix is between about 10 and about 30 parts by weight of the drug.

The drug can be any biologically active molecule that is suitable for being intimately admixed with the polymer without affecting the bioavailability of the drug. The device can be used for general drug delivery of various medicaments, for example, anticancer agents, antibacterial agents, antifungal agents, antiviral agents, sedatives, anesthetics, analgesics, and other medicaments useful in pain management, obstretrics or gynecology. The drug delivery device may also be suitable for delivering peptides having useful biological activity. Proteins may also be suitable for being incorporated into the drug delivery device of the invention.

The delivery system can be manufactured in a wide range of shapes, sizes and forms for delivering the biologically active molecule. The systems can be made as devices including buccal and oral devices; vaginal and intrauterine devices of cylindrical, bullet, elliptical, circular, bulbous, bow or any other shape that lends itself to placement in the desired biological environment. The devices include ocular devices, which can have a doubly convex, concavo-convex, and the like. The dimensions of the ocular device can vary according the size of the eye and generally have a thickness of 0.1–4 mm. Other devices made according to the invention include, implants, anal, pessaries and prosthetic devices, artificial glands for dispensing the pharmaceutically active agent.

Modification of the disclosed embodiments to achieve additional polymeric materials will be apparent to those skilled in the art. Such substitution, modification, and change are within the purview of the scope and limitations of the present invention and do not depart from the spirit of the invention thereof. The foregoing will be better understood in connection with Examples, which are intended as an illustration of and not a limitation upon the scope of the invention.

EXAMPLES

Example 1

Preparation of Poly(Erucic Acid Dimer-Co-Sebacic Anhydride) and Sorbitan Monostearate Blends The poly(erucic acid dimer-co-sebacic anhydride) (1:1 w/w) co-polymer having a weight average molecular weight of 53,000 g/mol was prepared in accordance with methods described in U.S. Pat. No. 4,789,724. The poly(erucic acid dimer-co-sebacic anhydride) was allowed to equilibrate from −40° C. to room temperature in a dessicator. A 5 weight percent sample was prepared by adding 0.2 g sorbitan monostearate to 3.8 g co-polymer. The mixture was introduced into a DACA twin screw extruder at the following settings: cooling air supply was 40 psig; temperature was 70° C.; compounding speed was 100 r.p.m.; load was 57 Nm; and orifice was 1 mm. The sample melted and mixed for three minutes before it was extruded and placed in a dessicator.

A second 5 weight percent sample was prepared by adding 0.175 g sorbitan monostearate to 3.325 g co-polymer, assuming 0.5 g sample remained in the extruder. The mixture was melted and mixed for three minutes, then extruded and placed in a dessicator.

A 20 weight percent sample was prepared by adding 0.775 g sorbitan monostearate to 2.725 g co-polymer, assuming 0.5 g of 5 weight percent sample remained in the extruder. The mixture was introduced into the extruder, melted, mixed, and extruded as described previously.

A second 20 weight percent sample was prepared by adding 0.70 g sorbitan monostearate to 2.8 g co-polymer, assuming 0.5 g remained in the extruder. The mixture was introduced into the extruder, melted, mixed, and extruded as described previously.

Example 2

Preparation of Poly(Erucic Acid Dimer-Co-Sebacic Anhydride) and Sorbitan Monolaurate Blends The co-polymer, poly(erucic acid dimer-co-sebacic anhydride) (1:1 w/w) with weight average molecular weight of 53,000 g/mol, was allowed to equilibrate from −40° C. to room temperature in a dessicator. A 5 weight percent sample was prepared by adding 0.2 g sorbitan monolaurate to 3.8 g co-polymer. The mixture was introduced into a DACA twin screw extruder at the following settings: cooling air supply was 40 psig; temperature was 70° C.; compounding speed was 100 r.p.m.; load was 57 Nm; and orifice was 1 mm. The sample melted and mixed for three minutes before it was extruded and placed in a dessicator.

A second 5 weight percent sample was prepared by adding 0.175 g sorbitan monolaurate to 3.325 g co-polymer, assuming 0.5 g sample remained in the extruder. The mixture was melted and mixed for three minutes, then extruded and placed in a dessicator.

A 20 weight percent sample was prepared by adding 0.775 g sorbitan monolaurate to 2.725 g co-polymer, assuming 0.5 g of 5 weight percent sample remained in the extruder. The mixture was introduced into the extruder, melted, mixed, and extruded as described previously.

A second 20 weight percent sample was prepared by adding 0.70 g sorbitan monolaurate to 2.8 g co-polymer, assuming 0.5 g remained in the extruder. The mixture was introduced into the extruder, melted, mixed, and extruded as described previously.

Example 3

Preparation of Poly(Erucic Acid Dimer-Co-Sebacic Anhydride) and Sorbitan Trioleate Blends The co-polymer, poly(erucic acid dimer-co-sebacic anhydride) (1:1 w/w) with weight average molecular weight of 53,000 g/mol, was allowed to equilibrate from −40° C. to room temperature in a dessicator. A 5 weight percent sample was prepared by adding 0.2 g sorbitan trioleate to 3.8 g co-polymer. The mixture was introduced into a DACA twin screw extruder at the following settings: cooling air supply was 40 psig; temperature was 70° C.; compounding speed was 100 r.p.m.; load was 57 Nm; and orifice was 1 mm. The sample was melted and mixed for three minutes before it was extruded and placed in a dessicator.

A second 5 weight percent sample was prepared by adding 0.175 g sorbitan trioleate to 3.325 g co-polymer, assuming 0.5 g sample remained in the extruder. The mixture was melted and mixed for three minutes, then extruded and placed in a dessicator.

A 20 weight percent sample was prepared by adding 0.775 g sorbitan trioleate to 2.725 g co-polymer, assuming 0.5 g of 5 weight percent sample remained in the extruder. The mixture was introduced into the extruder, melted, mixed, and extruded as described previously.

A second 20 weight percent sample was prepared by adding 0.70 g sorbitan trioleate to 2.8 g co-polymer, assuming 0.5 g remained in the extruder. The mixture was introduced into the extruder, melted, mixed, and extruded as described previously.

All extruded samples were stored at −40° C. until further studies were performed on them.

Example 4

Determination of the Molecular Weights of the Pure and Blended Co-polymers

The molecular weights of the pure and blended polymer samples were determined using gel permeation chromatography (gpc). Samples were prepared according to the method described in Examples 1, 2 and 3. The gel permeation chromatograph (Waters 2690 separations module with Waters 410 detector) was first calibrated with 8 polystyrene standards of molecular weights ranging from 400 to 1,300,000 g/mol. The eluent was methylene chloride. The flow rate was 1 milliliter per minute.

The extruded blends were allowed to equilibrate from −40° C. to room temperature in a dessicator. Approximately 35 mg from each sample were dissolved in 2 mL filtered methylene chloride. The resulting solution was filtered again into a scintillation vial and placed in the auto sampler tray. The samples were injected immediately following dissolution.

Example 5

Monitoring Molecular Weight Loss of the Co-polymers

The molecular weight loss of the co-polymers containing effective concentrations of the accelerants of degradation was monitored by gel permeation chromatography. A control molecular weight was obtained by gel permeation chromatography before any sample was subjected to stability testing.

A sample of extruded co-polymer with no additives and the extruded blends were placed inside individual open plastic bags inside a dessicator. The dessicator was placed in a room with a controlled temperature of 25° C.

After 96 hours, 168 hours, 264 hours, and 336 hours, approximately 50 mg of each sample were removed from the controlled environment. The molecular weights were determined by gel permeation chromatography. These weights were compared to the molecular weights of the controls and to the molecular weight of the pure, unblended co-polymer. The results of the monitoring are summarized in FIG. 3.

Figure 3:
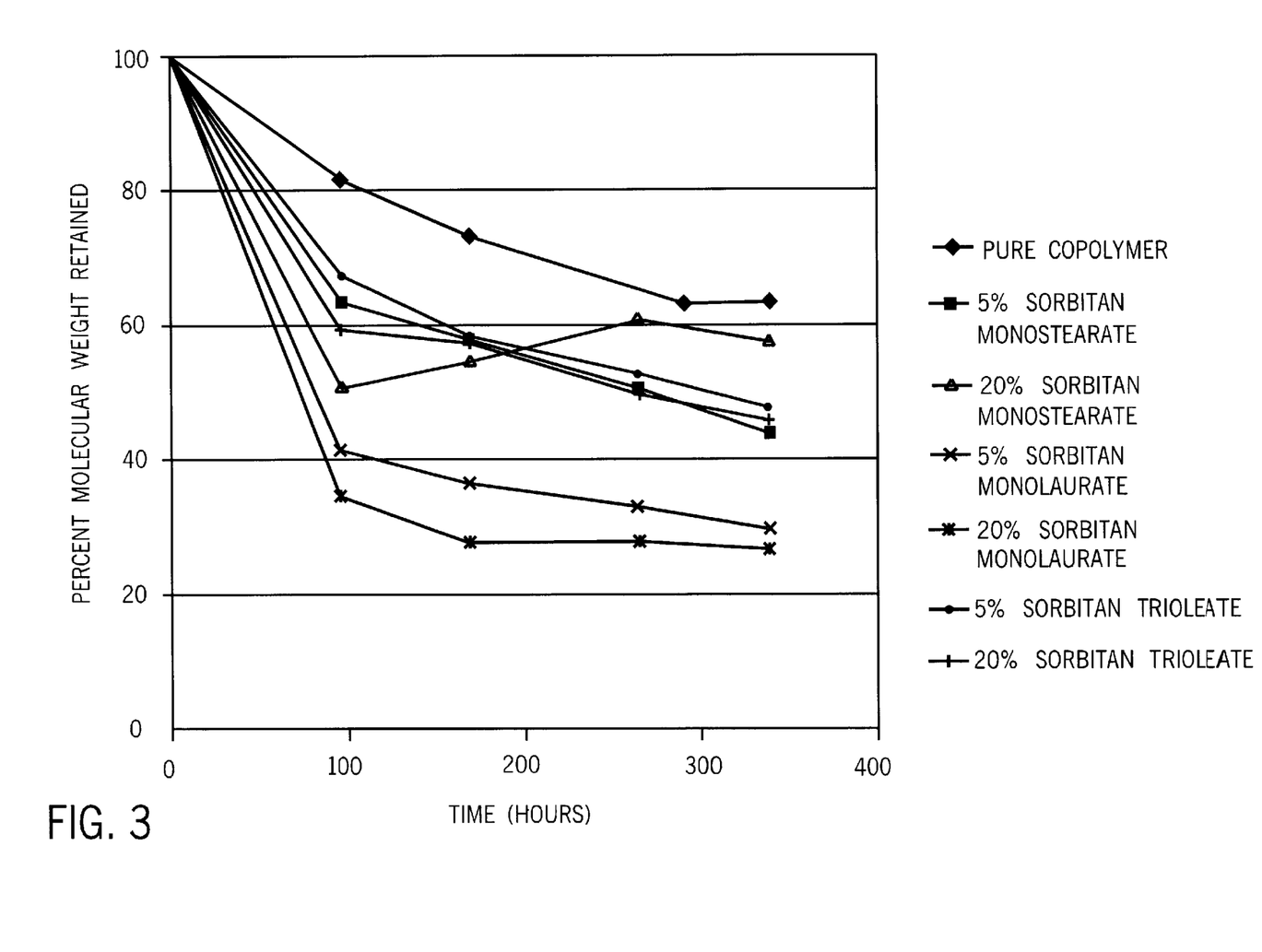
FIG. 3 is a graph illustrating the percent molecular weight retained of a pure polyanhydride co-polymer and various co-polymer blends having accelerant additives as a function of time (in hours) under dessicator conditions (anhydrous calcium oxide and magnesium sulfate dessicant) at 25° C.

As demonstrated in FIG. 3, the additives accelerate the degradation of the poly(erucic acid-co-sebacic anhydride) co-polymer. Sorbitan monostearate, sorbitan monolaurate, and sorbitan trioleate increase degradation of the co-polymer up to 30% at 25° C. and limited humidity.

Example 6

Analysis of Additives Having a Retardant Effect on the Degradation of the Pure and Blended Polymers The following samples were prepared in accordance with the methods described in Example 1:20% paraffins, 20% polyethylene glycol (PEG 1000), and 20% polyethylene glycol methyl ether (PEG Methyl Ether 5000). The samples and the pure polymer blend were placed in a controlled conditions having a temperature of 25° C. and 40% humidity. The determination of the molecular weights and the monitoring of the weight loss in the polymer were carried out in the manner described in Examples 4 and Example 5, respectively. The accompanying graph of FIG. 4 shows the extent of stabilization of the polymeric matrix at the indicated concentrations of the additives.

As demonstrated in FIG. 4, the additives retard the degradation of the poly(erucic acid-co-sebacic anhydride) co-polymer. The retarding effect of the additives results in up to 15% of stabilization of the polymeric matrix.

Example 7

Determination of Diluent Effect

A sample was prepared in accordance with Example 1, but substituting 5% titanium dioxide, by weight, for the additive. The molecular weight of the polymer blend was determined and the weight loss monitored in accordance with Examples 4 and 5, respectively. The loss of the molecular weight of polymeric matrix having no titanium dioxide was compared with the loss of molecular weight in the polymeric matrix with 5% titanium dioxide. Results are reported below in Table 1.

TABLE 1

| Time hours | 0% $TiO_2$[1] | 5% $TiO_2$[1] |
|---|---|---|
| 0 | 100 | 100 |
| 72 | 94 | 73 |
| 216 | 97 | 65 |
| 384 | 100 | 55 |
| 720 | 95 | 51 |

[1]The results are reported in percent number average molecular weight.

The stabilization is not a simple diluent effect as demonstrated by the reported results in Table 1.

What is claimed is:

1. A bioerodible polymeric composition, comprising poly (erucic acid dimer-co-sebacic anhydride) and a pharmaceutically acceptable additive, wherein the additive affects the rate of degradation of the poly(erucic acid dimer-co-sebacic anhydride).

2. The bioerodible polymeric composition according to claim 1, wherein the additive is a chemically non-reactive compound.

3. The bioerodible polymeric composition according to claim 2, wherein the chemically non-reactive compound is paraffin.

4. The bioerodible polymeric composition according to claim 3, comprising about 1 to about 20 percent by weight of the paraffin.

5. The bioerodible polymeric composition according to claim 4, comprising about 5 percent by weight of the paraffin.

6. The bioerodible polymeric composition according to claim 4, further comprising a medicament or a biologically active molecule.

7. The bioerodible polymeric composition according to claim 6, wherein the medicament is an anticancer agent, antibacterial agent, antifungal agent, antiviral agent, sedative, anesthetic, or analgesic.

8. A controlled medicament delivery device, comprising poly(erucic acid dimer-co-sebacic anhydride) and a pharmaceutically acceptable additive, wherein the additive affects the rate of degradation of the poly(erucic acid dimer-co-sebacic anhydride).

9. The controlled medicament delivery device according to claim 8, wherein the additive is a chemically non-reactive compound.

10. The controlled medicament delivery device according to claim 9, wherein the chemically non-reactive compound is paraffin.

11. The controlled medicament delivery device according to claim 10, comprising about 1 to about 20 percent by weight of the paraffin.

12. The controlled medicament delivery device according to claim 10, comprising about 5 percent by weight of the paraffin.

13. The controlled medicament delivery device according to claim 12, further comprising a medicament or a biologically active molecule.

14. The controlled medicament delivery device according to claim 13, wherein the medicament is an anticancer agent, antibacterial agent, antifungal agent, antiviral agent, sedative, anesthetic or analgesic.

15. A method for modifying the degradation rate of poly(erucic acid dimer-co-sebacic anhydride), comprising blending the poly(erucic acid diner-co-sebacic anhydride) with a pharmaceutically acceptable additive.

16. The method according to claim 15, wherein the additive affects the rate of degradation of the poly(erucic acid dimer-co-sebacic anhydride).

17. The method according to claim 16, wherein the additive interacts with the poly(erucic acid dimer-co-sebacic anhydride) in a manner which decreases the rate of degradation of the poly(erucic acid dimer-co-sebacic anhydride).

18. The method according to claim 17, wherein the pharmaceutically acceptable additive comprises a compound that is chemically non-reactive.

19. The method according to claim 18, wherein the additive is paraffin.

20. The method according to claim 19, wherein the paraffin is present in about 1 to about 20 weight percent relative to the weight of the poly(erucic acid dimer-co-sebacic anhydride).

21. The method according to claim 20, wherein the paraffin is present in about 5 weight percent relative to the weight of the poly(erucic acid dimer-co-sebacic anhydride).

22. The method according to claim 21, comprising the steps of:
   (a) melting the poly(erucic acid dimer-co-sebacic anhydride) at a temperature above its the glass transition temperature; and
   (b) adding paraffin to and blending the paraffin with the poly(erucic acid dimer-co-sebacic anhydride).

* * * * *

UNITED STATES PATENT AND TRADEMARK OFFICE
CERTIFICATE OF CORRECTION

PATENT NO.   : 6,503,528 B1
DATED        : January 7, 2003
INVENTOR(S)  : Christopher Bieniarz et al.

It is certified that error appears in the above-identified patent and that said Letters Patent is hereby corrected as shown below:

<u>Title page,</u>
Item [57], ABSTRACT,
Line 1, replace "The invention relates to a bioerodible polymeric composition, a method of making such a composition, and a controlled delivery device comprising the composition." with -- The invention relates to a bioerodible polymeric composition comprising poly(erucic acid dimer-co-sebacic anhydride) and a pharmaceutically acceptable additive, wherein the additive affects the rate of degradation of the poly(erucic acid dimer-co-sebacic anhydride), a method of making such a composition, and a controlled delivery device comprising the composition. --

Signed and Sealed this

Seventeenth Day of June, 2003

JAMES E. ROGAN
*Director of the United States Patent and Trademark Office*